United States Patent
Krasnow et al.

(10) Patent No.: US 10,316,171 B2
(45) Date of Patent: Jun. 11, 2019

(54) THERMAL STABILIZATION OF POLYMERS USING FUNCTIONALIZED PARTICLES OF TRANSITION METAL COMPOUNDS

(71) Applicant: Agienic, Inc., Tucson, AZ (US)

(72) Inventors: Nicholas R. Krasnow, Tucson, AZ (US); Anoop Agrawal, Tucson, AZ (US); Donald R. Uhlmann, Tucson, AZ (US)

(73) Assignee: Agienic, Inc., Tucson, AZ (US)

( * ) Notice: Subject to any disclaimer, the term of this patent is extended or adjusted under 35 U.S.C. 154(b) by 0 days.

(21) Appl. No.: 14/850,784

(22) Filed: Sep. 10, 2015

(65) Prior Publication Data

US 2015/0376379 A1    Dec. 31, 2015

Related U.S. Application Data

(63) Continuation-in-part of application No. 14/089,146, filed on Nov. 25, 2013, now Pat. No. 9,155,310.

(60) Provisional application No. 62/066,488, filed on Oct. 21, 2014, provisional application No. 61/881,318, filed on Sep. 23, 2013.

(51) Int. Cl.

| | |
|---|---|
| *C08L 77/00* | (2006.01) |
| *C08K 9/02* | (2006.01) |
| *C08L 39/06* | (2006.01) |
| *C08L 33/02* | (2006.01) |
| *C08K 9/04* | (2006.01) |
| *A01N 59/20* | (2006.01) |
| *C09K 8/524* | (2006.01) |
| *C09K 8/54* | (2006.01) |
| *A61K 47/02* | (2006.01) |

(52) U.S. Cl.
CPC ............... *C08K 9/04* (2013.01); *A01N 59/20* (2013.01); *A61K 47/02* (2013.01); *C08L 33/02* (2013.01); *C08L 39/06* (2013.01); *C08L 77/00* (2013.01); *C09K 8/524* (2013.01); *C09K 8/54* (2013.01)

(58) Field of Classification Search
None
See application file for complete search history.

(56) References Cited

U.S. PATENT DOCUMENTS

| | | |
|---|---|---|
| 2,705,227 A | 5/1955 | Stamatoff |
| 3,438,935 A | 4/1969 | Leu |
| 3,440,210 A | 4/1969 | Blount et al. |
| 3,491,042 A | 1/1970 | Hermann |
| 3,519,595 A | 7/1970 | Hermann |
| 3,870,680 A | 3/1975 | Schurdak |
| 3,931,103 A | 1/1976 | Hardy |
| 4,172,069 A | 10/1979 | Cordes et al. |
| 4,745,006 A | 5/1988 | Mohajer |
| 4,902,299 A | 2/1990 | Anton |
| 5,180,402 A * | 1/1993 | Kubota ............ D01F 1/103 428/323 |
| 2,013,027 A1 | 10/2013 | Lurya et al. |
| 9,034,354 B2 | 5/2015 | Renne et al. |
| 2006/0194910 A1* | 8/2006 | Miyatake ............ B82Y 30/00 524/432 |
| 2006/0199900 A1* | 9/2006 | Matsumoto ......... B82Y 30/00 524/556 |
| 2009/0186971 A1* | 7/2009 | Grant ................. C08J 5/18 524/300 |
| 2009/0281210 A1* | 11/2009 | Aramaki ............ C08J 3/226 523/351 |
| 2011/0252580 A1* | 10/2011 | Miller ............ D06M 11/42 11/42 |
| 2015/0021528 A1* | 1/2015 | Chartoff ............ G02B 1/04 252/582 |

FOREIGN PATENT DOCUMENTS

CA         2776363 A1 *   4/2011   ............ A61L 31/16

OTHER PUBLICATIONS

ICL Industrial Products, "Potassium Bromide Powder", published Mar. 2014, p. 1-2.*
Aerogel.org, "Functionalizaton," <http://www.aerogel.org/?p=1918>, published Sep. 3, 2011, p. 1-3.*
Fujimori, Y. et al., "Novel Antiviral Characteristics of Nanosized Copper(I) Iodide Particles Showing Inactivation Activity against 2009 Pandemic H1N1 Influenza Virus," Appl. Environ. Microbiol. 2012, 78(4):951-955, Published Ahead of Print Dec. 9, 2011.*
"Incorporate," Merriam-Webster Online Dictionary, <https://www.merriam-webster.com/dictionary/incorporate>, published Apr. 23, 2009, p. 1.*
Janssen, K., Gijsman, P., Tummers D., Mechanistic aspects of the stabilization of polyamides by combinations of metal and halogen salts, Polymer Degradation and Stability, vol. 49 (1995) p. 127-133.
Cerruti, P., Carfagna, C., Thermal-oxidative degradation of polyamide 6,6 containing metal salts, Polymer Degradation and Stability, vol. 95 (2010) p. 2405-2412.

* cited by examiner

*Primary Examiner* — Monica A Shin
(74) *Attorney, Agent, or Firm* — Rothwell, Figg, Ernst & Manbeck, P.C.

(57) ABSTRACT

This invention is directed towards additives for improving the thermal stability of polymers. The additives comprise low water solubility particles of transition metal compounds which are surface functionalized. A specific additive for nylons utilizes surface functionalized CuI particles and may also contain alkali metal halides.

14 Claims, No Drawings

THERMAL STABILIZATION OF POLYMERS USING FUNCTIONALIZED PARTICLES OF TRANSITION METAL COMPOUNDS

CROSS REFERENCE TO RELATED APPLICATIONS/CLAIM OF PRIORITY

This application claims priority to provisional application Ser. No. 62/066,488 filed on Oct. 21, 2014, and is a continuation-in-part of co-pending U.S. application Ser. No. 14/089,146 filed on Nov. 25, 2013 which in turn claims priority to Provisional Patent Application Ser. No. 61/881,318 filed on Sep. 23, 2013. All of the foregoing applications are incorporated by reference herein.

BACKGROUND OF INVENTION

Thermal stabilization of polymers is carried out in several ways. Some of the important methods are by using additives which act as radical scavengers and/or decompose hydroperoxides which are formed by the reaction of oxygen and the polymers. It has been known that transition metal compounds, and in particular copper compounds along with alkali halides, are routinely used for stabilization of polymers, particularly polyamides or nylons and in some cases other polymers such as polyolefins. Mechanisms of stabilization in the literature suggest that these materials work by radical scavenging, decomposition of hydroperoxides and by reduction in oxygen uptake by the polymers. This action preserves the molecular weight of the polymer and also associated properties, which are impacted by either polymeric chain breakdown, formation of conjugated groups or by their branching/crosslinking, etc. Many of the copper compounds which are used, such as CuI, CuBr and CuCl, are added as bulk particles and then usually melt blended, or are added when the polymers are formed, such as during condensation polymerization of nylons at high temperature. The focus of the present invention is to provide the transition metal compounds in a form so that they are easy to blend with the polymers and form thermally stable compositions. Thermal stability allows these polymers to be used at elevated temperature applications without losing their mechanical, optical, electrical or other properties. In some cases these may also improve or impart flame retardant properties.

SUMMARY OF INVENTION

The focus of this invention is to provide particles of copper compounds which can more easily be dispersed into polymeric matrices. The materials are formed so that the particles are surface functionalized, wherein the functionalization provides superior compatibility/dispersability when the particles are blended into polymeric matrices and thereby enhances their processability (miscibility) and/or stabilization performance.

DETAILED DESCRIPTION OF THE EMBODIMENTS OF THE INVENTION

Thermal stabilization additives are routinely used for polymers. Transition metal compounds, and in particular copper compounds along with alkali halides are routinely used for stabilization of polymers, particularly polyamides or nylons and in some cases other polymers such as polyolefins. In order for these materials to disperse uniformly and quickly in the polymeric matrices, it is advantageous that they be incorporated as particles, which are surface functionalized. The nature of the surface functionalization is dependent on the polymeric matrix.

Some of the preferred transition metal compounds are those of Co, Cu, Ni and Zn, of which the halides and oxides are most preferred. The most preferred transition metal compounds have low water solubility (less than about 100 mg/liter at room temperature). In nylons these materials may be combined with water soluble alkali halides (e.g., KI, NaI, etc.). The transition metal compounds are added in low concentrations, typically between 10 to 500 ppm (as metal concentration by weight in the polymeric composition); and in many cases the use of these low concentrations does not impart any color to the composition. More generally, it is desirable that the additives not impart any undesired coloration to the product in the concentrations at which the additives are effective as thermal stabilizing agents.

One way to measure color for products comprising these compositions is by employing a colorimeter and using standard color coordinates such as L*a*b*. An L* value of 100 (maximum) indicates a completely white color and a value of 0 indicates a completely black color. Increasing negative values of a* indicate increasing green color and increasing positive values indicate red. Increasing negative values of b* indicate increasing blue color and increasing positive values indicate yellow. Comparing a product with the additive and without the additive, the difference in any one of the values of L*, a*, or b* should be less than about ±5 units and more preferably less than about +−2 units. Preferred compounds for providing enhanced thermal stabilization of polymers, especially polyamides, with minimal coloration are cuprous compounds, and more preferably cuprous halides selected from CuI, CuBr and CuCl, of which CuI is most preferred.

In some polymers, for example in polyolefins, the presence of certain transition metal compounds such as several copper compounds can increase thermal degradation. For such polymers when particles of copper-containing materials are added (e.g., using particles of copper compounds to impart antimicrobial properties) the polymers should be thermally stabilized against degradation which may be caused by these particles. One method of doing this is by functionalizing the particles using agents which are typically used as additives to prevent thermal degradation in these polymers. Such functionalizing agents may be chosen from compositions known to stabilize polyolefins in the presence of copper (e.g., see U.S. Pat. Nos. 3,931,103; 3,870,680; 3,438,935, 3,440,210 as examples). These include mixtures of hindered phenols and materials containing nitrogen. Some of the nitrogen-containing polymers which may be used as functionalization agents with copper salts are those with amide groups including polyamides and PVP or its copolymers.

The size of the particles may be any, but a preferred average size range is below 1,000 nm, and more preferably below 300 nm. One may also mix particles with different average sizes and even particles of more than one transition metal compound, e.g., different copper halides, or a copper halide and a zinc halide, etc.

Functionalization agents may be polymeric or nonpolymeric and are generally organic materials. These agents have a molecular weight of at least 60, preferably at least 80 and most preferably at least 100. More than one functionalization agent may be used in an additive composition.

Both synthetic and natural polymers may be used as functionalization agents. Synthetic polymers include polyvinyl pyrrolidone (PVP) and its copolymers. PVP copolymers means all polymers which have segments of polymerized vinyl pyrrolidone, e.g., block copolymers, graft copolymers, alternating copolymers, random copolymers, etc. The copolymers may have both hydrophobic and hydrophilic sequences. Preferred comonomers for PVP copolymers are caprolactam, olefins and vinyl acetate. Examples of PVP/polyolefin copolymers with varying amount of hydrophobicity are Ganex® WP-660, Ganex® V-516 and Ganex® P904LC available from Ashland (New Milford, Conn.). More examples of other synthetic polymeric surface functionalization agents include polyvinyl acetate, poly(vinyl alcohol) (PVA), polyamides (nylons, polyacrylamides), polyacrylic/methacrylic acid, copolymers of acrylic acid (including methacrylic acid), soluble cellulosics (e.g., carboxy methyl cellulose), polyacrylamide, polyethylene glycols and polypropylene glycols or oxides (and their polymers and copolymers), polyolefins modified with maleic anhydride (e.g., OREVAC® polymers from Arkema Group, King of Prussia, Pa.), ionic polymers (cationic or anionic), polymers with alcoholic groups, urethanes and epoxies. As taught in several places in this specification, block and graft (including comb-like) copolymers are suitable under a variety of circumstances as they can provide good compatibility and dispersion characteristics. One may also use biodegradable polymers and copolymers such as polylactic acid) PLA) and polyglycolic acid (PGA) comprising polymers. The natural polymers include carbohydrates (starch) and its components (amylose and amylopectin), chitosan, glycogen and protein based polymers.

The polymers to be stabilized may be also used as functionalization agents. The molecular weight of the functionalization polymer is preferably less than the molecular weight of the polymer being stabilized, and more preferably less than half the molecular weight of the polymer being stabilized. For example, a polyamide polymer may be stabilized with particles that are functionalized using a polyamide polymer of smaller molecular weight.

When using block or graft copolymers, one may advantageously use those materials where sections in the copolymer have different properties in terms of ionic characteristics or their attraction/compatibility with desired matrices. For example, one block or graft may be hydrophobic or ionic, and another block or another graft or the main polymer chain may be hydrophilic or non-ionic, etc. Some examples of copolymers which may be used for functionalization are polyethylene glycol (PEG) and polypropylene glycol (PPG) dimethicones, sodium laureth-13 carboxylate, copolymer of methyl vinyl ether and maleic anhydride, bisamino PEG/PPG 41/3 aminoethyl PG-propyl dimethicone, amine functionalized silicones (amidomethicone) and block copolymers of PEG and PPG (e.g., triblock copolymer with various block lengths such as Pluronics™ available from BASF, Germany). Some of the block copolymers with hydrophilic and hydrophobic blocks are also considered as non-ionic surfactants as discussed below.

Each of the above polymers may have a range of molecular weights, typically in the range of about 1,500 to 1,000,000 Daltons, although molecular weights less than 200,000 are preferred, and molecular weights less than 100,000 are most preferred. Several functionalization agents may be used together in the same formulation, and some of them may be polymeric and others non-polymeric.

Embodiments of the invention also make use of surfactants for surface functionalization agents. Surfactants represent an important class of functionalization agents as they form a bridge or a link between hydrophobic and hydrophilic surfaces or matrices. The term surfactants includes nonionic, cationic, anionic and amphoteric surfactants, some specific examples being Brij®, Tween® (polysorbate), Triton® X-100, Igepal®, Merpol® (all of these registered products being available from Sigma Aldrich, Milwaukee, Wis.), benzethonium, benzalkonium, dimethyldialkylonium, alkylpyridinium and alkyltrimethylammonium cations with any anion, e.g., bromide, chloride, acetate or methyl sulfate, silicone-ethylene oxide/propylene oxide copolymers (e.g., OFX-0190, OFX-0193 and OFX-5329 from Dow Corning, Midland, Mich.), Sodium dodecyl sulfate (SDS), sodium capryl sulfonate, sodium lauryl sulfate, sodium laureth sulfate, cetyltrimethylammonium chloride or cetyltrimethylammonium bromide (all available from Sigma-Aldrich Co, Milwaukee, Wis.), silicone surfactants, fluorosurfactants (e.g., Novec surfactants from 3M (St. Paul, Minn.) such as FC-4430, FC-4432, FC-4434 and FC-5120), salts of organic acids. Other surfactants include fatty alcohol ethoxylates, alkyl phenol athoxylates, phosphate esters, acetylene diols (e.g., ethoxylated acetylene diols), salts of polyacrylic acid (e.g., sodium salts of polyacrylic acid) and soy lecithin. Anionic, amphoteric and nonionic surfactants are preferred, and anionic and non-ionic surfactants are most preferred. Natural or bio-engineered surfactants may be used.

Functionalization agents may also comprise acids. Some of these acids include acetic acid, stearic acid, citric acid, glutamic acid, lactic acid, tartaric acid, glycolic acid, malic acid, thiodipropionic acid, sulfamic acid, gallic acid, alginic acid, caprylic acid, linoleic acid, cinammic acid and alkylbenzene sulfonic acids, such as dodecyl benzene sulfonic acid. Typically acids with room temperature water solubility of greater than about 100 mg/liter are preferred.

Salts of many of the above acids (particularly those containing cations of lithium, sodium, potassium, zinc and copper) and esters of organic salts of the above acids may also be employed as additives and may be used as functionalization agents. Some examples of alkali salts of are mono, di and tri-sodium citrates, sodium cinnamonate, sodium lactate, sodium palmitate, sodium oleate, sodium formate, calcium diacetate, sodium gluconate, sodium carboxy methyl cellulose, sodium caseinate zinc gluconate and zinc stearate.

For stabilizing polyamide polymers (nylons) one may use diacids as part of the functionalization agent package. These acids may be aliphatic acids, aromatic acids, or acids with unsaturated groups. Some examples of these diacids are adipic acid, sebacic acid, butanedioic acid, maleic acid and fumaric acid. Typically the additive compositions comprising functionalized particles should have less than 20% and preferably less than 10% by weight of acids.

In some cases, the functionalization agents may use a multiple tier approach, where the particles are functionalized using a first material, and then this mixture is treated with a formulation containing a second material, where the second material may further functionalize the particles by interacting with the still-exposed particle surface or reacting/interacting with the end groups of the first functionalization material (i.e. the first functionalization material can behave as a linker). This sequence may be repeated multiple times. To serve as linkers, the preferred materials are surfactants or those which have at least two reactive or interactive sites on the material. Preferred examples of linkers (or monomers) with functionality equal or greater than two include silanes with specific organic groups such as acrylic, epoxy, amine, acidic groups, isocyanates (e.g., diisocyantes), polyols (e.g., diols such as ethyelene diol and polyethylene oxide diol), polyacids (diacids such as adipic acid, sebaccic acid), materials with reactive hydroxyl and acid groups along with vinyl groups (e.g., acrylic polyols, methacrylic polyols), etc.

An important embodiment of the present invention is the functionalization of the low water solubility metal salt particles which are used as thermal stabilizers. Such particles are preformed and functionalized before they are added to the polymeric matrices. In functionalizing the surfaces of the particles, molecules are attached either chemically or physically to the surfaces. These functionalizing agents should be present while the particles (or the new surfaces) are being formed, either during chemical synthesis, precipitation from solutions, or during physical grinding (when the particles are being ground to a finer size from larger particles). Many of these methods are described in U.S. patent application Ser. No. 14/089,146, filed on Nov. 25, 2013, which is incorporated herein by reference). The amount of surface functionalizing agent increases with decreasing particle size in proportion to the overall change in surface area exposed for functionalizing. A wide range in the relative amounts of the metal salt particles and the functionalizing material may be used. In typical additive compositions of this invention, the weight ratios (low water solubility metal salt:functionalizing agent) are in a range of about 1000:1 to about 1:100 and more preferably a range of about 100:1 to 1:20. Using higher molecular weight functionalization agents helps to weaken the interaction between the particles and helps with dispersion in matrix polymers.

The functionalized particles may be synthesized or formed in a liquid medium containing the functionalization agents. One preferred method is wet-grinding to form the functionalized particles uses bead mills. Wet media mills are available from several sources such as NETZSCH Fine Particle Technology, LLC., Exton Pa. (e.g., Nanomill Zeta®); Custom Milling and Consulting, Fleetwood, Pa. (e.g., Super Mill Plus); Glen Mills Inc, Clifton N.J. (e.g., Dyno® Mill) and bead mills (e.g., DMQX-10) from Union Process, Inc, Akron, Ohio. These mills typically comprise chambers in which hard ceramic or metal beads (grinding media) are vigorously stirred along with liquid slurries of the powders which result in grinding of the powders down to finer sizes. Preferred liquid (wet) media are aqueous. Preferred grinding media beads are about 1 mm or smaller and more preferably in the range of about 0.04 to 0.5 mm and most preferably 0.3 mm or smaller. Optionally, the grinding procedure may start with a larger grinding bead size to grind initially the large particles to a smaller particle size and then using smaller grinding beads perhaps in a different equipment to reduce the particle size further. In this case, functionalization agents may be present at each of the stages or only in as few as one of them (as the final stage).

In a typical process, low water solubility salts (e.g., CuI) are added to these mills in water. The surface functionalization agents may be present in the beginning or added later (while the grinding is still being carried out). One may also add functionalization agents incrementally as the grinding proceeds. When more than one functionalization agent is present, then these may be added together, or they may be added at different times in the processing. Also when alkali metal halides are used (which are generally water soluble), these may also be added in the desired proportion into the grinding chamber. Again these may be present at the beginning or may be added during the process. Some of the alkali halides useful with CuI are Ki, NaI and LiI. Other halides for use with CuBr are preferably KBr, NaBr and LiBr, and for use with CuCl preferably KCl, NaCl and LiCl. These alkali halides may work both as processing aides during grinding (if the functionalized particles are made in this fashion) and also work as co-stabilizers against heat in the polymers to which these compositions are added to. Additional alkali halides (even an alkali halide of a different composition) may also be added to the polymeric matrices.

Once the grinding process is over, then one can dry this slurry to obtain the additive. The polymer to be stabilized and these dry additives can be melt blended using standard techniques such as using a roll mill or on a twin screw extruder. Higher concentrations of these additives may be used to produce master batches, which are then mixed with polymers during further processing to lower their concentration to the desired amount in the final product. Another method of blending these materials to form master batches is to spray (or treat) polymer beads with these liquid slurries, drying these beads and then taking them through the melt blending process.

Workers in the production facility should be protected from small airborne particles when drying these slurries or coated pellets. For this it is important to minimize the possibility of getting the small particles airborne. An effective method of accomplishing this involves making the particle size of the dried powders containing many functionalized particles relatively large compared with the size of the individual functionalized particles. The particles of such dried powder particles will contain a number of the functionalized particles. The size of the dried powders should be greater than 1 micron, preferably greater than 10 microns, and most preferably greater than 100 microns. Such dry powders are easily handled and transported for downstream operations. To achieve this, the functionalization agent package comprises a polymeric binder (molecular weight greater than about 1,500 and preferably greater than about 8,000). This binder may also be a functionalization agent. When the slurries are sprayed onto polymeric beads or pellets and dried, these binders are act as film formers and bind the small functionalized particles together as pellets. During master batch formation or melt blending, the binder melts or dissolves and the smaller functionalized particles disperse easily and uniformly into the matrix. The binder used should be such so that it has a melting or dissociation temperature lower than the melting or processing temperature of the polymer being stabilized and also be compatible with the polymeric matrix. In addition, it is also preferred that the binder have a lower viscosity (when melt processed) as compared to the polymer being stabilized so that the functionalized particles disperse easily.

Further, one may form a thermal stabilizer additive package which includes functionalized particles and other additives. The other additives include additional thermal stabilizers (co-stabilizers), colorants, oxidative stabilizers, UV stabilizers, dispersion aids, processing aids, etc. It is preferred that all of these are added and mixed in a master batch, which contains a polymeric matrix similar to or the same polymer for which this additive package is intended. Typically the concentration of the ingredients in the master batch is such that when about 5 to 10% of the masterbatch is used to add to the polymeric materials to make products, the concentration of the thermal stabilizers and other co-additives ends up in the desired concentration.

A particularly useful co-additive for use in additive package with the metal halide based thermal stabilizers of this invention are alkali halides. Particularly preferred are halides of Li, Na and K. The most preferred halides are LiI, NaI and KI. Typically the concentration of these is from about 0.1 to about 5,000 ppm by weight of the polymeric composition. The compositions may comprise more than one alkali halide. For nylons when CuI is used as the thermal stabilizer, the concentration of the alkali halides is typically in the range of about 2 to 10 times of the thermal stabilizer.

EXAMPLES

Example 1: Preparation of PVP Functionalized CuI Particles by Wet Grinding in Water The samples for heat stabilizing nylon (e.g., nylon 6; nylon 6,6; nylon 4,10; nylon 4,6; nylon 6,10, nylon 11, nylon 12, etc.) were prepared in a wet grinding mill produced by Netzsch Premier Technologies LLC (Exton Pa.), equipment model was Minicer®. The grinding beads were 3M™ Micro Milling Media ZGC ceramic (100 μm in diameter). The interior of the mill was also ceramic lined. Copper iodide, sodium iodide, polyvinvylpyrrolidone (PVP) K17 (Molecular weight Mw=9,000 (weight average molecular weight), Mn=2,000 (number average molecular weight), adipic acid, polyacrylic acid (MW=1800), and deionized water were combined in compositions as indicated in Table 1 below. These materials were processed at a mill speed of 4200 RPM and recirculation pump speed of 600 RPM for 360 minutes.

TABLE 1

| Sample | CuI (g) | NaI (g) | PVP (g) | Adipic Acid (g) | Polyacrylic acid (g) | Water (g) |
|---|---|---|---|---|---|---|
| A | 9 | 0.1 | 0.45 | 0.45 | | 200 |
| B | 9 | 0.1 | 0.45 | | 0.45 | 200 |
| C | 8 | 1 | 0.5 | | 0.5 | 200 |
| D | 9 | 0.1 | 0.9 | | | 200 |

Samples A-D resulted in stable dispersions with minimal settling. All dispersions were dryable to form free flowing powders. All of the dispersions formed transparent films with little or no color, when dried on a glass microscope slide, which showed that the size of the functionalized particles was below about 100 nm. This indicates that the prepared samples A-D would not impact the coloration of a polymer to which it would be added, and would disperse easily in the matrix. Typical commercial nylons have an average molecular weight in excess of 10,000. Sample D was melt blended very uniformly with a nylon polymer without imparting any coloration to the nylon.

Example 2: Preparation of Functionalized CuI Particles Using an Alcohol Soluble Nylon Samples were prepared using an alcohol soluble polyamide polymer to prepare surface functionalized copper iodide particles. Elvamide 8061 is an alcohol soluble polyamide polymer (obtained from DuPont, Wilmington, Del.). Elvamide 8061 and PVP (if present) was dissolved in ethanol prior to mixing or milling processes in the proportions shown in Table 2. The mill and the grinding conditions for samples E and F were the same as described in Example 1.

Sample G was prepared by taking a portion of ground and dried sample D from Example 1 in ethanol and further adding Elvamide 8061 in a round bottom flask. The solution was stirred for 24 hours and dried to obtain the additive.

TABLE 2

| Sample | CuI (g) | NaI (g) | PVP (g) | Elvamide 8061 | Ethanol (mL) |
|---|---|---|---|---|---|
| E | 90 | 1 | 9 | 11.1 | 200 |
| F | 90 | | | 10 | 200 |
| G | 90 | 1 | 9 | 11.1 | 400 |

Samples E through G resulted in stable dispersions with minimal settling. All of the dispersions had measured particle sizes of less than 100 nm as measured by dynamic light scattering. All dispersions were dryable to form purple polymeric material. The melting point of Elvamide was not reduced during the grinding/mixing processes as measured by differential scanning calorimetry; in all cases the melting point was maintained around 155° C.

Example 3: Preparation of Functionalized CuI Particles Using a Water-Soluble Nylon Samples were prepared using a water-soluble polyamide polymer to prepare copper iodide particles. AQ Nylon (P70) is a water-soluble polyamide polymer (obtained from Toray, North Kingston, R.I.). AQ Nylon and PVP (when present) were dissolved in water prior to the start of the milling processes. The mill and the grinding conditions for samples H and I in Table 3 were the same as described in Example 1.

Sample J was prepared by taking a portion of ground and dried sample D from Example 1 in ethanol and further adding Elvamide 8061 in a round bottom flask. The solution was stirred for 24 hours and dried to obtain the additive.

TABLE 3

| Sample | CuI (g) | NaI (g) | PVP (g) | AQ NYLON | Water (mL) |
|---|---|---|---|---|---|
| H | 90 | 1 | 9 | 11.1 | 200 |
| I | 90 | | | 10 | 200 |
| J | 90 | 1 | 9 | 11.1 | 400 |

Samples H-J resulted in stable dispersions with minimal settling. All of the dispersions had measured particle sizes of less than 100 nm as measured by dynamic light scattering. All dispersions were dryable to form purple polymeric material, which could be formed in pellets/flakes. The melting point of AQ Nylon was not reduced during the grinding/mixing processes as measured by differential scanning calorimetry.

Example 4: Preparation of Nylon Functionalized CuI Particles by Synthesis

In a round bottom flask 7.88 mL of a 2000 ppm copper (cupric (II) chloride) aqueous solution and 0.78 mL of 20 wt % AQ Nylon aqueous solution were mixed. Then 10.0 mL of 4000 ppm iodide (sodium iodide) aqueous solution was added and mixed. An additional 5.0 mL of 4000 ppm iodide (sodium iodide) aqueous solution was added and mixed to drive the reaction to completion. Addition of NaI caused CuI particles to form, which were then collected using centrifugation and washed with water.

The invention claimed is:
1. A method of thermally stabilizing a polymer comprising:
 a) providing an additive comprising preformed particles of a copper salt having a room temperature water solubility of less than about 100 mg/liter and particle size less than about 1000 nm, b) surface-modifying said particles with a functionalization agent, wherein said functionalization agent is added at a ratio of said copper salt to said functionalization agent of about 1000:1 to about 1:100 to form a preformed and functionalized additive;

c) providing a polymer, and d) dispersing a thermally-stabilizing amount of said preformed and functionalized additive in said polymer wherein the thermally-stabilizing amount of said preformed and functionalized additive is configured to react with compounds produced by decomposition of said polymer to form a thermally-stabilized polymer, wherein said preformed and functionalized additive thermally stabilizes the polymer and reduces at least one of (a) polymer scission; (b) polymer branching; (c) crosslinking of polymer; and (d) conjugation formation in said thermally-stabilized polymer compared to the polymer without said additive.

2. The method of claim 1, wherein the thermally-stabilized polymer has a difference in any one of L*, a*, or b* values that is less than plus or minus 5 units compared to a polymer without said particles.

3. The method of claim 1, wherein the additive comprises preformed particles of a Cu halide.

4. The method of claim 3, wherein the halide is CuI.

5. The method of claim 1, wherein the polymer is a nylon polymer.

6. The method of claim 5, wherein said functionalization agent is a nylon polymer with a molecular weight less than the molecular weight of the nylon polymer being stabilized.

7. The method of claim 1, wherein said functionalization agent comprises a nitrogen containing material.

8. The method of claim 1, wherein the molecular weight of the functionalization agent is at least 60.

9. The method of claim 8, wherein the functionalization agent is selected from at least one of a polymer, a surfactant, an organic acid and a monomer.

10. The method of claim 8, wherein said functionalization agent is a nylon polymer.

11. The method of claim 1, wherein the additive further comprises at least one alkali metal halide.

12. A method of thermally stabilizing a polymer comprising:

a) providing an additive comprising preformed particles of a copper salt having a room temperature water solubility of less than about 100 mg/liter and particle size less than about 1000 nm, b) surface-modifying said particles with a functionalization agent to obtain a preformed and functionalized additive, c) providing a polymer, and d) dispersing a thermally-stabilizing amount of said preformed and functionalized additive in said polymer wherein the thermally-stabilizing amount of said preformed and functionalized additive is configured to react with compounds produced by decomposition of said polymer to form a thermally-stabilized polymer, wherein said preformed and functionalized additive thermally stabilizes the polymer and reduces at least one of (a) polymer scission; (b) polymer branching; (c) crosslinking of polymer; and (d) conjugation formation in said thermally-stabilized polymer compared to the polymer without said additive.

13. The method of claim 12, wherein the additive comprises preformed particles of CuI.

14. A method of thermally stabilizing a nylon polymer comprising:

a) providing an additive comprising preformed surface-functionalized particles of copper iodide with particle size less than about 1000 nm, b) providing a nylon polymer, and c) dispersing a thermally-stabilizing amount of said additive in said nylon polymer wherein the thermally-stabilizing amount of said additive is configured to react with compounds produced by decomposition of said nylon polymer to form a thermally-stabilized nylon polymer, wherein said additive thermally stabilizes the nylon polymer and reduces at least one of (a) polymer scission; (b) polymer branching; (c) crosslinking of polymer; and (d) conjugation formation in said thermally-stabilized polymer compared to the nylon polymer without said additive.

* * * * *